(12) United States Patent
Laupper

(10) Patent No.: US 7,753,585 B2
(45) Date of Patent: Jul. 13, 2010

(54) X-RAY DEVICE HAVING A COLUMN AND HAVING A CANTILEVER ARM DISPLACEABLE ON THE COLUMN

(75) Inventor: Ruedi G. Laupper, Hitzkirch (CH)

(73) Assignee: Swissray International Inc., Elizabeth, NJ (US)

( * ) Notice: Subject to any disclaimer, the term of this patent is extended or adjusted under 35 U.S.C. 154(b) by 213 days.

(21) Appl. No.: 11/918,727

(22) PCT Filed: Nov. 17, 2005

(86) PCT No.: PCT/EP2005/056027

§ 371 (c)(1),
(2), (4) Date: Oct. 18, 2007

(87) PCT Pub. No.: WO2006/111210

PCT Pub. Date: Oct. 26, 2006

(65) Prior Publication Data

US 2009/0067580 A1 Mar. 12, 2009

(30) Foreign Application Priority Data

Apr. 19, 2005 (WO) ................ PCT/EP2005/051727

(51) Int. Cl.
*H05G 1/02* (2006.01)
*G03B 42/04* (2006.01)

(52) U.S. Cl. ................. 378/197; 378/167; 378/189; 378/193; 378/196

(58) Field of Classification Search .............. 378/167, 378/189, 193, 196, 197
See application file for complete search history.

(56) References Cited

U.S. PATENT DOCUMENTS

| | | | | |
|---|---|---|---|---|
| 2,217,262 A * | 10/1940 | Tunnicliffe | ............... | 378/58 |
| 3,250,583 A * | 5/1966 | Phillips | ............... | 433/27 |
| 3,293,632 A * | 12/1966 | Blume | ............... | 52/32 |
| 3,694,653 A * | 9/1972 | Allard et al. | ............... | 378/178 |
| 4,115,695 A * | 9/1978 | Kelman | ............... | 378/17 |
| 4,115,696 A * | 9/1978 | Truscott | ............... | 378/13 |
| 4,741,014 A * | 4/1988 | Lajus | ............... | 378/189 |
| 4,813,064 A * | 3/1989 | Jackson et al. | ............... | 378/197 |
| 5,008,920 A * | 4/1991 | Gralak | ............... | 378/185 |
| 5,469,492 A | 11/1995 | Burbury et al. | | |
| 5,636,259 A * | 6/1997 | Khutoryansky et al. | ..... | 378/197 |
| 5,652,781 A * | 7/1997 | Armbruster et al. | ......... | 378/182 |
| 5,901,200 A | 5/1999 | Krause | | |

(Continued)

FOREIGN PATENT DOCUMENTS

EP 0 927 891 A2 7/1999

*Primary Examiner*—Edward J Glick
*Assistant Examiner*—Thomas R Artman
(74) *Attorney, Agent, or Firm*—The Nath Law Group; Jerald L. Meyer; Sungyeop Chung

(57) ABSTRACT

The invention relates to an X-ray device (1) provided with a column (2) and an arm which is upwardly (3) displaceable therealong and on which at least one X-ray picture detector (4) and/or an X-ray transmitter (5) are mounted. A receiving means (6) arranged on the column is used for receiving a picture carrier (7) on the plane part (8). Preferably, said receiving means is embodied in the form of a support for interchangeably receiving the picture carrier in such a way that large-surface images are placeable on the column without affecting the arm operation.

16 Claims, 7 Drawing Sheets

U.S. PATENT DOCUMENTS

Figure 1:
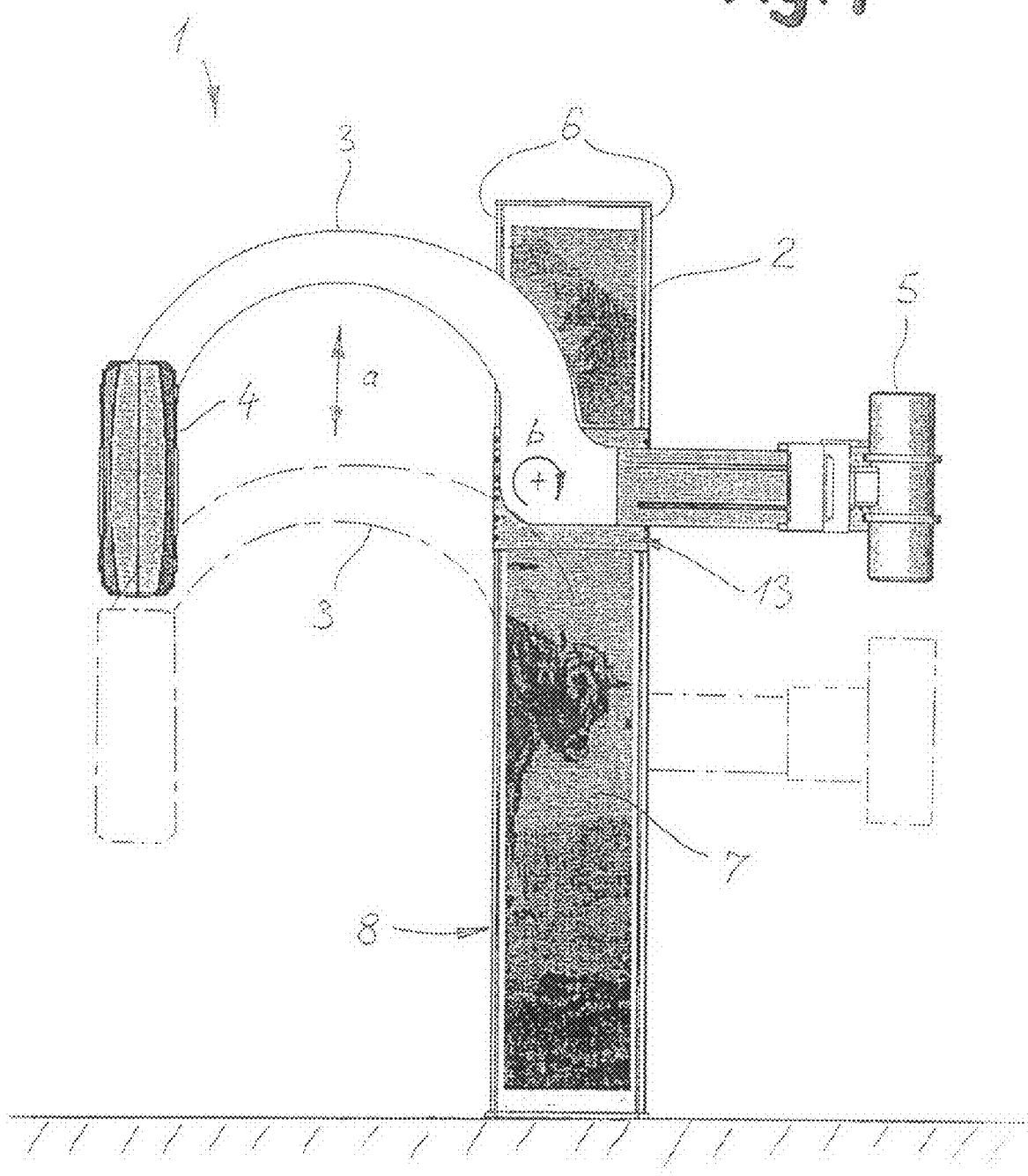

| | | | |
|---|---|---|---|
| 6,851,851 B2 * | 2/2005 | Smith et al. | 378/189 |
| 7,469,032 B2 * | 12/2008 | Walker et al. | 378/38 |
| D604,415 S * | 11/2009 | Otsuka et al. | D24/158 |
| 2002/0126470 A1 | 9/2002 | Saito et al. | |
| 2003/0223549 A1 * | 12/2003 | Winsor et al. | 378/189 |

* cited by examiner

X-RAY DEVICE HAVING A COLUMN AND HAVING A CANTILEVER ARM DISPLACEABLE ON THE COLUMN

The invention relates to an X-ray device having a column and having a cantilever arm whose height can be displaced on the column according to the preamble of claim 1. Such X-ray devices are used today to produce X-ray images and/or real time X-ray film sequences for various diagnostics purposes. The cantilever arm can be, for example, a C arm that enables different positionings on lying, standing or sitting patients. The X-ray image detector is currently mostly provided for producing digital X-ray images.

X-ray devices are mostly set up centrally in a room, the column forming an eyecatcher. However, there is the need to use the column as an information medium for images or characters. These can be changing patient information, advertising messages, or simply only decorative elements. In the case of generically comparable conventional X-ray devices, however, the column cannot be used for such purposes. It is therefore an object of the invention to provide an X-ray device in the case of which it is possible to fix on the column graphic displays that are as far as possible large in area and preferably interchangeable. A further object of the invention consists in designing the guidance and the neuromechanism for the displacement of the cantilever arm such that a coherent surface section that is as large as possible remains on the column. There is also the aim to improve the accessibility of the components arranged in the interior of the column.

This object is achieved according to the invention with the aid of an X-ray device that has the features in claim 1. The mounting means on the column enable an image carrier to be mounted on a specific surface section of the column. What can be involved here is a plane, or else a concavely or convexly curved surface. The mounting means is here advantageously a holder, that can be fixed on the column, for the preferably interchangeable mounting of the image carrier. The holder can in this case form a type of picture frame into which the image carrier can be pushed or clamped in the manner of a quick change picture frame.

With particular advantage, the holder has a cover made from transparent material for protecting the image carrier. The cover can, for example, consist of acrylglass or of silica glass. It would be conceivable in specific instances to use one side of the cover directly as image carrier.

In order to attain a particular effect, the holder can have a light for the purpose of illuminating the image carrier. Light-emitting diodes (LEDs) have proved to be particularly advantageous. These can be arranged in the edge region of the holder such that they radiate light laterally into the holder. Here, it can be possible for the light from the light-emitting diodes to be fed laterally into a diffuser plate that is arranged down-stream of the image carrier. The diffuser plate distributes the light over the entire image surface. Moreover, the illumination effect can be further improved by arranging a reflector plate on the side of the diffuser plate averted from the image carrier. The reflector plate casts the light distributed in the diffuser plate forward onto the image carrier.

However, the holder could also include an image screen or a display for the alternating display of images or characters. Thus, it would be conceivable, for example, to integrate a flat display screen or a light crystal display in the holder. It is possible in this way also to display rapidly alternating image sequences and/or film sequences. This could render it possible, for example, for a patient himself to view X-ray pictures of himself while they are being taken.

The holder can essentially extend over the entire width and height of the column such that practically an entire front side of the column can accept an image carrier.

A particularly advantageous presentation of the image carrier can be achieved when the cantilever arm has a guide carriage that overlaps the surface section and that is preferably guided on the column behind the mounting means on the side averted from the image carrier. This type of guidance makes the entire area of the surface section available without interfering slots, guide rails or the like. Moreover, a more stable and smoother guidance is achieved that could also be advantageous for the mounting of an image carrier in conjunction with conventional X-ray devices without mounting means.

The guide carriage can in this case be guided on two parallel guide rails that are, however, covered by the image carrier and are therefore not visible from the outside. Guidance on the guide rails could be performed in this case via skids or via rolling contact bearings.

In order to displace the cantilever arm on the column, it is possible to arrange on the guide carriage a rack that meshes with a pinion which is supported on the column and can be driven by a drive motor. This type of drive has the advantage that less mass need be accelerated and decelerated, since the drive motor is permanently flanged to the column. The rack can be dimensioned in length such that it is still respectively just in engagement with the pinion in the lowermost and uppermost positions of the cantilever arm. The rack/pinion gear is in this case advantageously arranged between the two guide rails. Moreover, it is expedient for the rack to be supported on the rear side in the engagement region of the pinion, in order to avoid sagging, particularly in the region of the end positions.

The guide carriage can, moreover, have lateral guide cheeks that are connected to a guide plate that can be displaced behind the image carrier. This guide plate can have skids that are guided on the two parallel guide rails. Thus, for example, two skids arranged at a distance from one another can be provided per guide rail. The load of the cantilever arm is thus distributed as uniformly as possible over the guides.

Further advantages can be attained when the cantilever arm is fastened on the carriage in a way capable of being pivoted away laterally from an operating position into a dismantling position, this being done in such a way that in the dismantling position the holder can be dismantled approximately at right angles to the movement plane of the carriage. For this purpose, the cantilever arm can be fastened on a hinged plate that, as component of the guide carriage can be displaced at a distance from the image carrier and parallel thereto, and that is provided on one side with hinges for the pivoting movement.

The column itself can have an approximately cuboidal housing, the image carrier or the holder being designed as housing cover. In this way, the image carrier is seen to fulfill a double function. It serves for decorative purposes, on the one hand, and on the other hand facilitates the accessibility of the components inside the column, in order to be able to execute maintenance and repair work.

The image carrier itself can be associated with completely different materials or designs. For example, it would be conceivable to have a flat plate made from metal, plastic, wood, cardboard or some other material that is provided on one side with a graphic display. The latter can be applied using various printing techniques, photomechanical methods or the like. However, the image carrier could also be a frame that is covered, for example, with a textile or other sheetlike structure. The image carrier could also have a relief-like surface structure, or it could be designed in such a way that specific optical effects are attained such as, for example, the effect of a three-dimensional image display. Finally, the image carrier could also be a flat container filled with liquid or with a gas, it being possible to attain specific color effects, lighting effects or the like.

When the image carrier is an advertising medium, the column of the X-ray device can be used as an illuminating advertising pillar on which various advertising messages can be displayed. Such an X-ray device is suitable, for example, for use in sponsoring as a marketing measure in the medical field. Financing or cofinancing of an X-ray device by a sponsor can be displayed on the image carrier in a particularly simple way.

Figure 2:
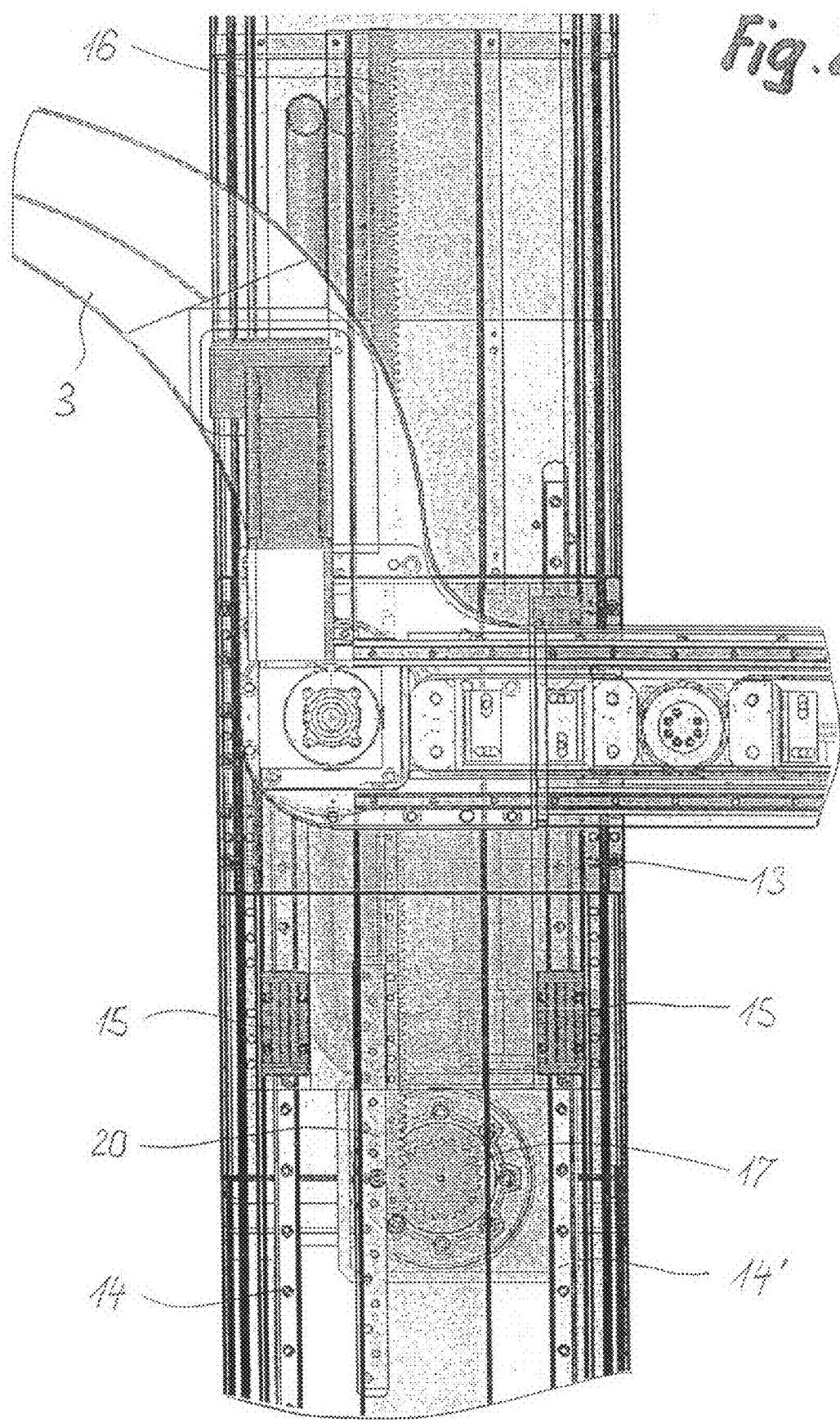
Figure 3:
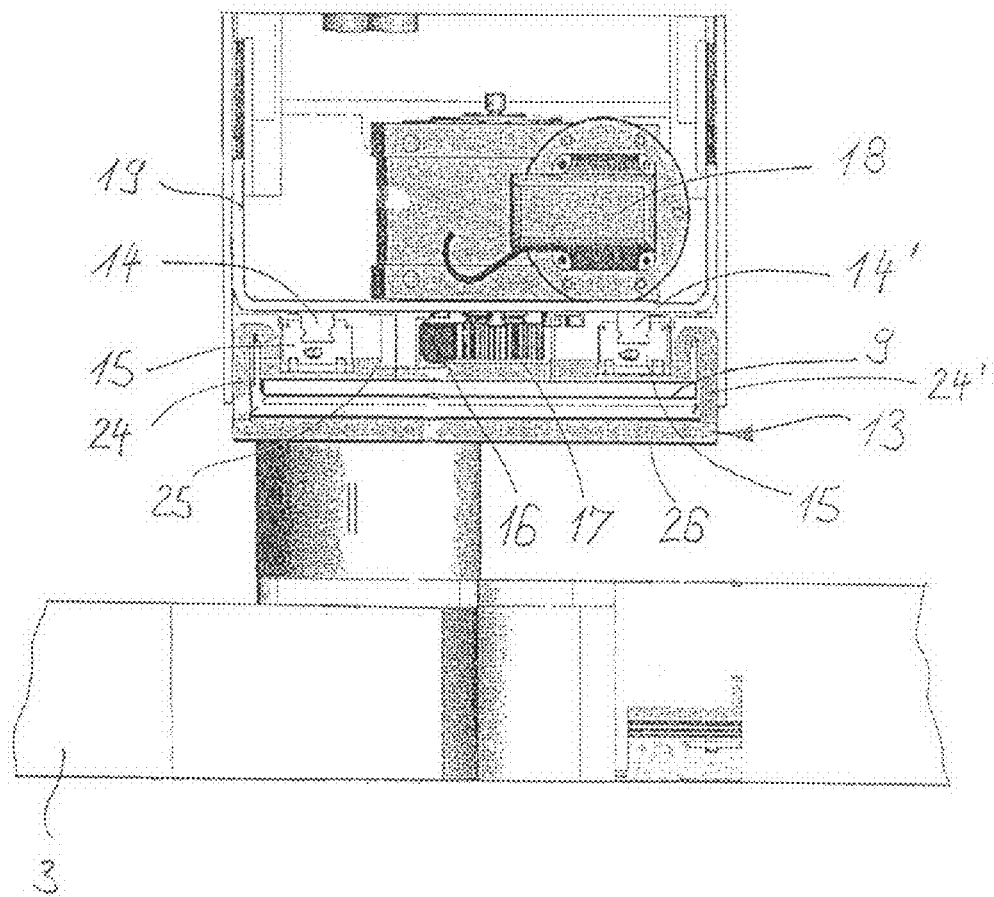
Figure 6:
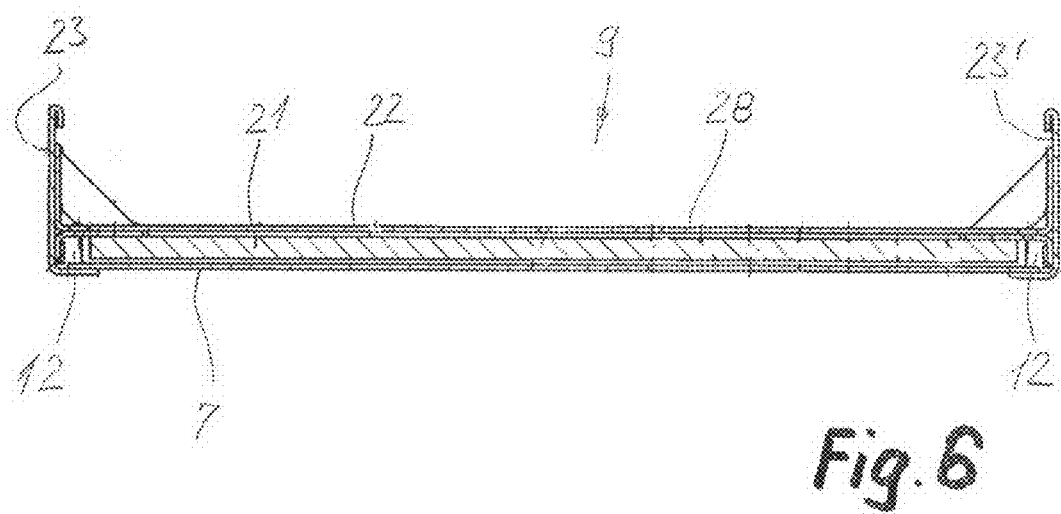
Figures 4, 5:
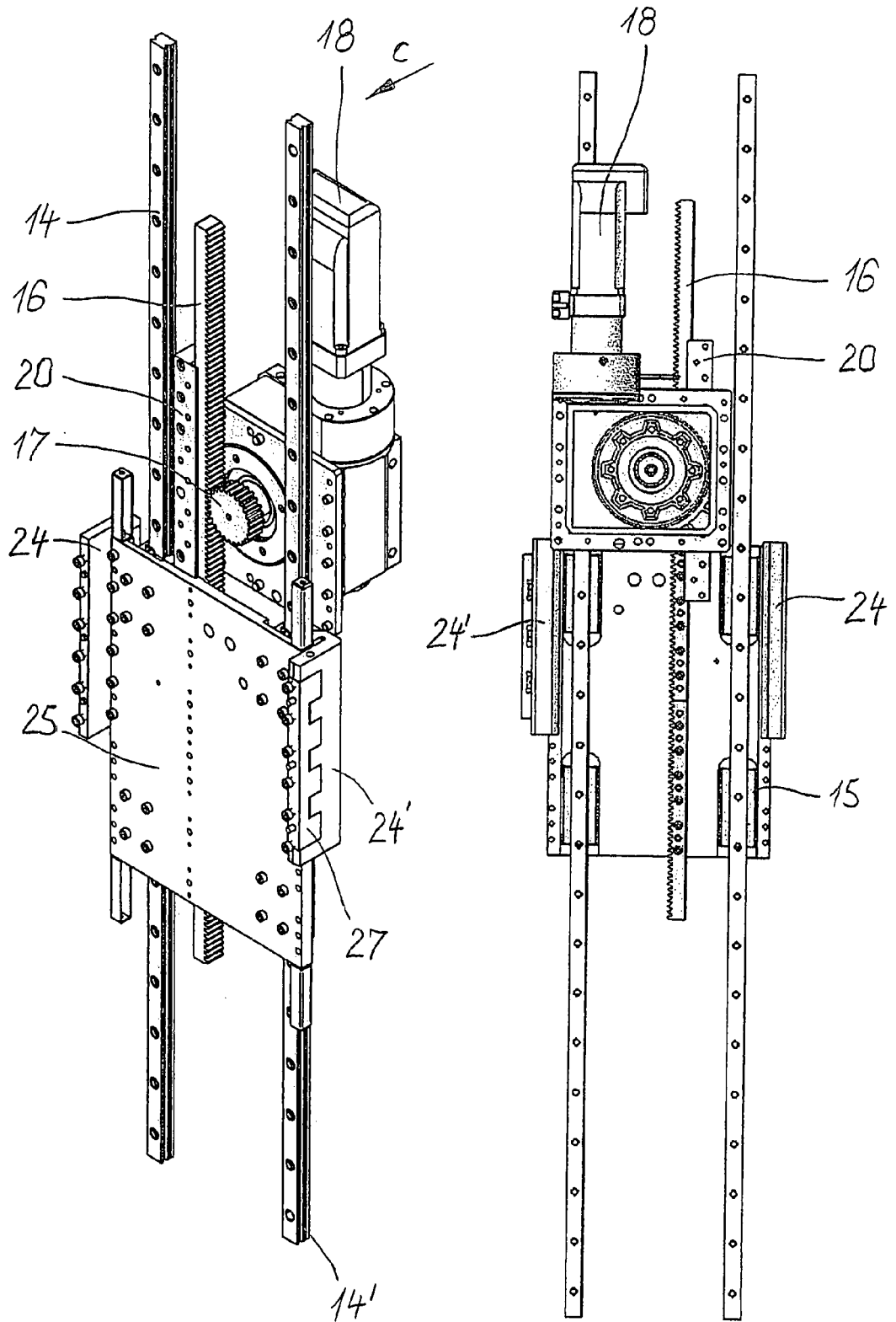
Figure 7:
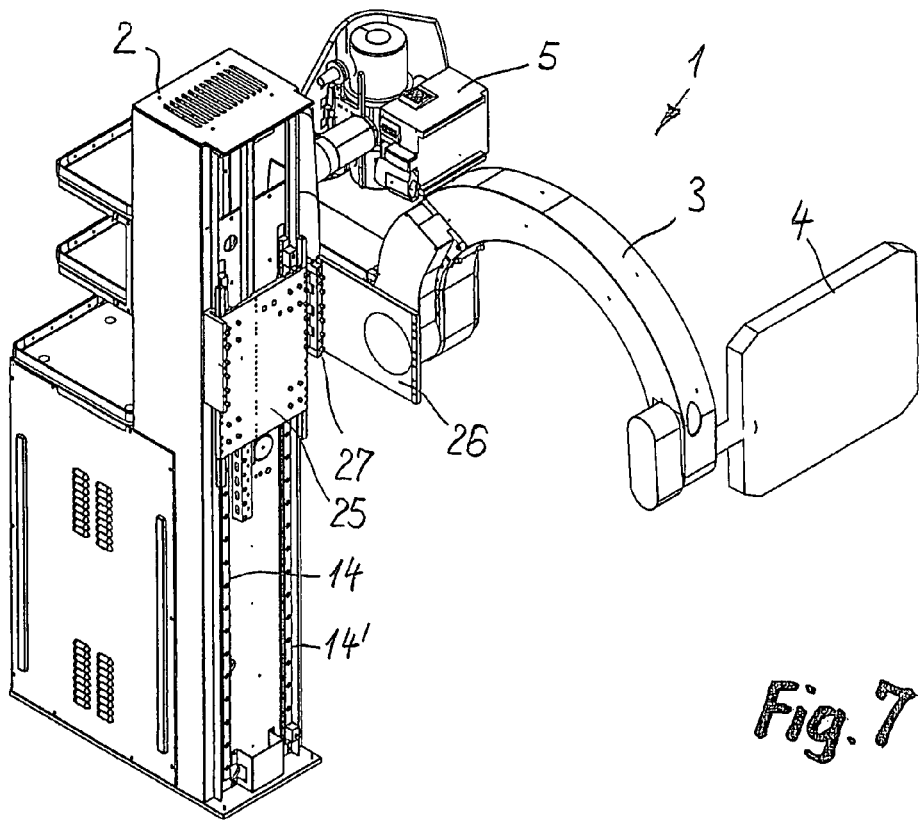
Figure 8:
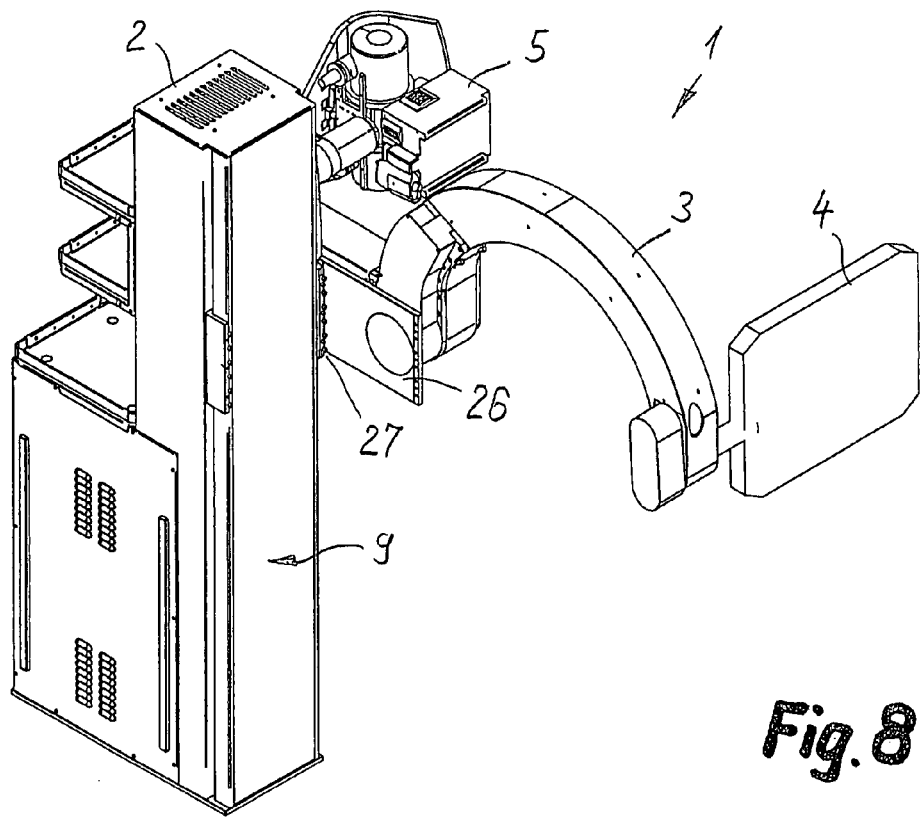
Figure 9:
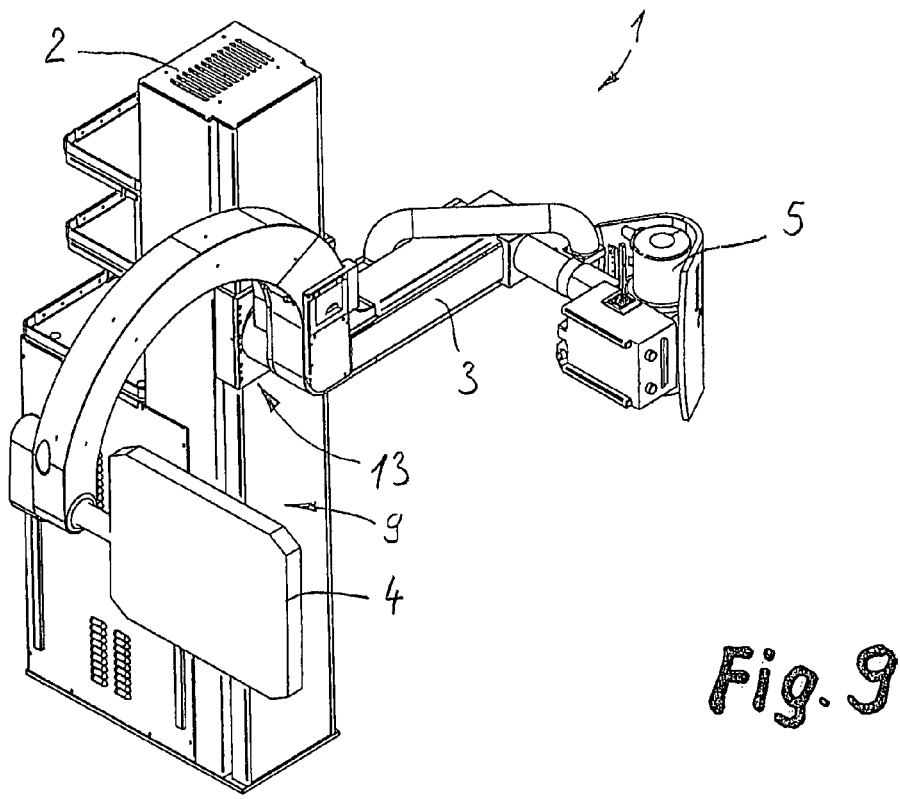
Figure 10:
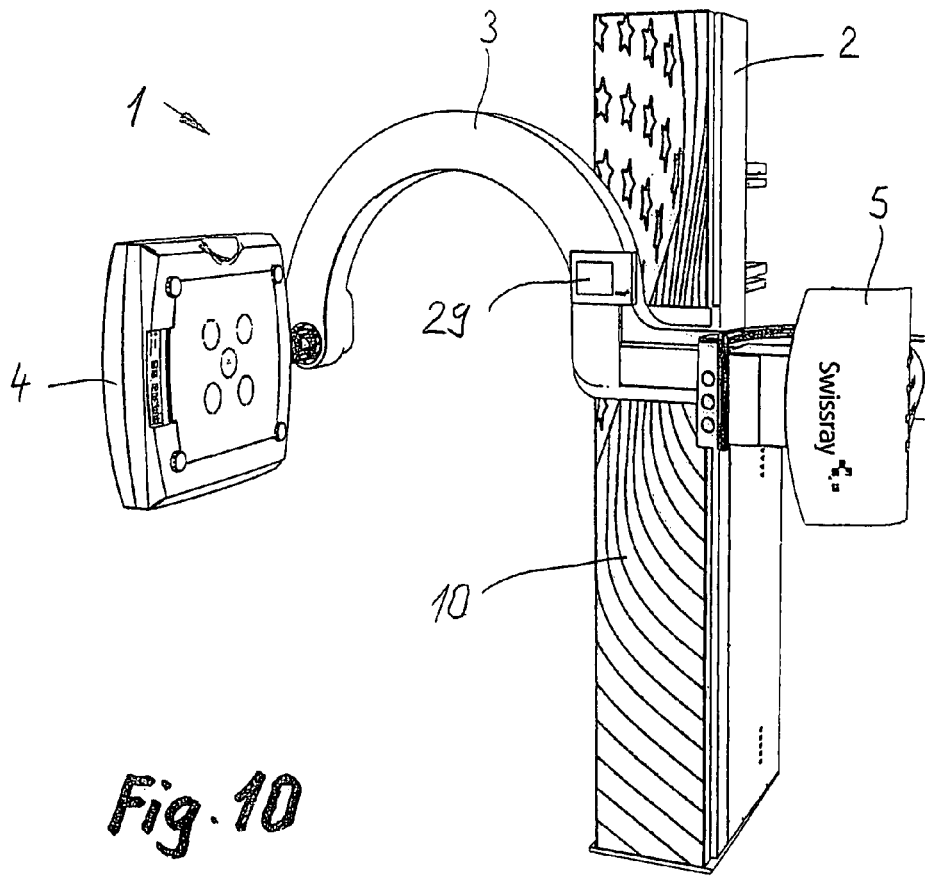
Figure 11:
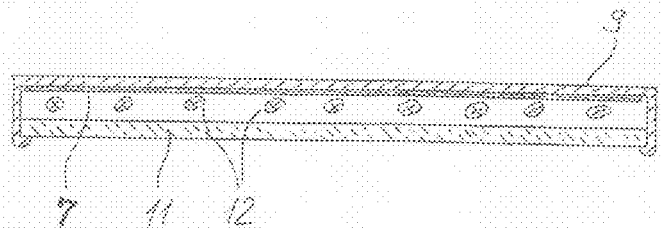
Figure 12A:
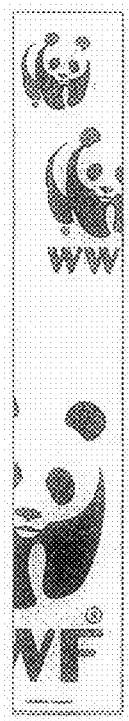
Figure 12B:

Further advantages and individual features of the invention emerge from the drawings and from the following description of an exemplary embodiment. In the drawings:

FIG. 1 shows a view of an X-ray device having a column and cantilever arm,

FIG. 2 shows the region where the cantilever arm is guided on the column, in enlarged illustration, FIG. 3 shows a plan view of the column in accordance with FIG. 2, FIG. 4 shows a perspective illustration of the gear arrangement for the height adjustment of the cantilever arm, FIG. 5 shows a rear view, from the arrow direction c, of the arrangement in accordance with FIG. 4, FIG. 6 shows a cross section through a holder with image carrier, FIG. 7 shows a perspective illustration of an X-ray device with the cantilever arm pivoted out, and with the holder dismantled, FIG. 8 shows the X-ray device in accordance with FIG. 7 with installed holder, FIG. 9 shows the X-ray device in accordance with FIG. 8 with the cantilever arm in operating position, FIG. 10 shows a perspective illustration of the X-ray device in accordance with FIG. 9, from another perspective, FIG. 11 shows a cross section through an alternative exemplary embodiment of a holder with image carrier, and FIGS. 12a and 12b show examples of an alternative image display.

In accordance with FIG. 1, an X-ray device 1 essentially comprises a column 2 and a cantilever arm 3 supported such that its height can be displaced on the column in the arrow direction a. The present exemplary embodiment is a C-shaped cantilever arm having a straight section, an X-ray image detector 4, for example a Bucky, being arranged on the end of the C bow, and an X-ray transmitter 5 being arranged on the end of the straight section. In addition, the cantilever arm 3 can also be swiveled about a horizontal axis in the arrow direction b. The guidance of the cantilever arm is performed with the aid of a guide carriage 13 whose details are still to be described below with the aid of FIGS. 2 to 5.

The column 2 has mounting means 6 for mounting an image carrier 7 on a surface section 8. In the present exemplary embodiment, the image carrier 7 contains a display of a picture that covers virtually the entire width and the entire height of the column 2.

As is to be seen from FIGS. 2 and 3, the guide carriage 13 is guided on two parallel guide rails 14, 14' that are arranged on a housing 19 of the column. In this case, the guidance is performed on skids 15 of which two are respectively provided per guide rail. The guide rails and the skids are configured in such a way that the skids are captive and slide with as little play as possible on the guide rails.

The mounting means for the image carrier essentially comprise a holder 9 that is held on the housing 19 of the column only at the lower and at the upper ends. On the side, the holder 9 is embraced by the guide carriage 13, and/or the guide cheeks 24 and 24'. The gear for the displacement of the cantilever arm 3 is also completely covered by the holder 9 in this way.

The two guide cheeks 24, 24', which are J-shaped in cross section, are connected to a guide plate 25 on which the skids 15 are also fastened. On the outer side, the two guide cheeks 24, 24' are connected by means of a hinged plate 26 that is pivoted to the guide cheek 24' on one side via a hinge 27. The hinged plate 26 is detachably screwed on the guide cheek 24. The cantilever arm 3 is fastened on the hinged plate 26.

The gear consists of a rack 16 that is assigned to the carriage 13. This rack meshes with a pinion 17 that is supported on the outer side on the housing 19. The pinion can be driven by a drive motor 18 in the interior of the housing 19. In order to avoid transverse forces causing sagging of the rack, the latter is supported by a support strip 20 in the region of the engagement with the pinion. This support strip is permanently arranged, and therefore assigned to the housing 19 like the guide rails 14, 14'. Rolling contact bearings can be installed in order to reduce the friction at the support strip 20.

FIGS. 4 and 5 show the entire guidance and gearing arrangement once again in a detached fashion. The hinged plate is, however, not illustrated here, but rather the hinge 27 is. The individual components of the carriage are respectively screwed to one another.

FIG. 6 shows a cross section through the holder 9 installed in accordance with FIG. 3. The structure made from steel plate or from plastic has side parts 23, 23' that extend over the entire height of the column and are embraced by the two J-shaped guide cheeks 24, 24'. The frame-like structure has a rear wall 28 on which a reflector plate 22 is arranged. Fastened on the reflector plate is a diffuser plate 21 that distributes the light fed in laterally from the light-emitting diodes 12 over the entire surface. The image carrier 7, made from a plexiglass plate, for example, is pushed in over the diffuser plate 21 and can easily be interchanged with the holder dismantled. The actual image is bonded as a film onto the rear side of the image carrier 7.

In accordance with FIG. 7, the cantilever arm 3 is pivoted up by approximately 90° on the hinged plate 26. The holder 9 provided with the image carrier can be installed in this position, something which is illustrated in FIG. 8. Subsequently, the cantilever arm 3 is pivoted back again into the operating position in accordance with FIG. 9, and the hinged plate 27 is screwed.

FIG. 10 shows the X-ray device from another perspective with a section from the US flag as actual image 10. Likewise to be seen is a monitor 29 that is fastened on the cantilever arm 3 and, for example, displays patient data.

In the case of the exemplary embodiment in accordance with FIG. 11, the image carrier 7 is fastened directly on the rear wall of the carrier 9. A cover 11 made from acrylglass protects the image carrier, and the illumination is performed by light-emitting diodes 12 or by other luminous means on the upper and the lower ends of the holder. However, it would also be conceivable here for the rear side or the front side of the cover 11 to take over the function of the image carrier directly. Thus, for example, a plotter could be used to print the image onto a transparent, self-adhesive film that is bonded directly onto the surface of the acrylglass plate. In such a case, the rear wall of the holder 9 serves as reflector for the illumination.

The luminous means can basically be driven such that the image carrier can be displayed smoothly as far as beaming illumination. Again, alternating colors or alternating light intervals can very easily be implemented with the aid of light-emitting diodes, in particular.

FIGS. 12a and 12b show alternative images 10 that could be used in the holders described. It is to be seen that a completely different optical effect is attained depending on selected image, without the need for any sort of structural changes on the device itself.

The invention claimed is:

1. An X-ray device comprising a column and a cantilever arm whose height is displaceable on the column, at least one X-ray image detector and/or at least one X-ray transmitter being arranged on the cantilever arm, wherein the device further comprises mounting means on the column for mounting an image carrier on a surface section of the column,
   wherein the mounting means is a holder, which is fixable on the column, for the mounting of the image carrier,
   wherein the cantilever arm includes a guide carriage that overlaps the surface section of the column and is guided on the column behind the mounting means on a side averted from the image carrier,
   wherein the cantilever arm is fastened on the carriage in a way being pivotable away laterally from an operating position into a dismounting position, in the dismounting position the holder being dismountable approximately at right angles to the movement plane of the carriage.

2. The X-ray device according to claim 1, characterized in that the holder includes a cover made from transparent material for protecting the image carrier.

3. The X-ray device according to claim 1, characterized in that the holder includes a light for illuminating the image carrier.

4. The X-ray device according to claim 3, characterized in that the light comprises a plurality of light-emitting diodes that extend over at least an edge region of the holder and light emission from the plurality of light-emitting diodes is fed laterally into a diffuser plate arranged downstream of the image carrier.

5. The X-ray device according to claim 4, characterized in that a reflector plate is arranged on a side of the diffuser plate averted from the image carrier.

6. The X-ray device according to claim 1, characterized in that the holder includes an image screen or a display for alternating display of images or characters.

7. The X-ray device according to claim 1, characterized in that the holder essentially extends over the entire width and height of the column.

8. The X-ray device according to claim 1, characterized in that the guide carriage is guided on two parallel guide rails.

9. The X-ray device according to claim 1, characterized in that arranged on the guide carriage is a rack that, for displacing the guide carriage, meshes with a pinion which is supported on the column and is driven by a drive motor.

10. The X-ray device according to claim 9, characterized in that a rack/pinion gear is arranged between the two guide rails.

11. The X-ray device according to claim 1, characterized in that the guide carriage includes lateral guide cheeks that are connected to a guide plate that is displaceable behind the image carrier.

12. The X-ray device according to claim 11, characterized in that the guide plate includes skids that are guided on the two parallel guide rails.

13. The X-ray device according to claim 1, characterized in that the cantilever arm is fastened on a hinged plate that, as a component of the guide carriage is displaceable at a distance from the image carrier and parallel thereto, and that is provided on one side with hinges for the pivoting movement.

14. The X-ray device according to claim 1, characterized in that the column includes an approximately cuboidal housing, and that the image carrier or the holder is designed as a housing cover.

15. The X-ray device according to claim 1, characterized in that the image carrier is a transparent plate made from acryl-glass, and the image is bonded as a film onto the plate.

16. The X-ray device according to claim 1, characterized in that the image carrier is an advertising medium.

* * * * *